US006987834B2

(12) United States Patent
Omernick et al.

(10) Patent No.: US 6,987,834 B2
(45) Date of Patent: Jan. 17, 2006

(54) OPTIMIZED RECORD TECHNIQUE SELECTION IN RADIOGRAPHY AND FLUOROSCOPY APPLICATIONS

(75) Inventors: Jon Charles Omernick, Wauwatosa, WI (US); Aluri Srinivas, Pewaukee, WI (US); Relihan F. Gary, Whitewater, WI (US); Preethi Kasthuri, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 185 days.

(21) Appl. No.: 10/248,330

(22) Filed: Jan. 9, 2003

(65) Prior Publication Data

US 2004/0136498 A1    Jul. 15, 2004

(51) Int. Cl.
    *H05G 1/46*    (2006.01)
(52) U.S. Cl. ...................... 378/109; 378/108
(58) Field of Classification Search ............... 378/95, 378/97, 108, 109, 110, 111, 112, 96
See application file for complete search history.

(56) References Cited

U.S. PATENT DOCUMENTS

| 4,748,648 A | * | 5/1988 | Boucle et al. ............... 378/97 |
| 6,222,907 B1 | * | 4/2001 | Gordon, III et al. ........ 378/116 |
| 6,233,310 B1 | * | 5/2001 | Relihan et al. ............. 378/108 |

FOREIGN PATENT DOCUMENTS

| JP | 54006485 A | * | 1/1979 |
| JP | 02078198 A | * | 3/1990 |

\* cited by examiner

*Primary Examiner*—Edward J. Glick
*Assistant Examiner*—Chih-Cheng Glen Kao
(74) *Attorney, Agent, or Firm*—Peter J. Vogel

(57) ABSTRACT

A method for regulating a scan dosage includes generating an initial technique command based on default patient size or the previous exposure and on completion of exposure, receiving the actual technique signal. A target entrance dose signal is determined based a default patient size, and tube current is regulated in response to the target entrance dose signal and dose feedback. Image brightness is independently controlled in response to the target entrance dose and average image brightness. An object size is estimated based on the actual technique signal and an image brightness feedback. An optimized generator technique is defined based on estimated object size to achieve a target image quality for the user selected contrast material.

13 Claims, 4 Drawing Sheets

OPTIMIZED RECORD TECHNIQUE SELECTION IN RADIOGRAPHY AND FLUOROSCOPY APPLICATIONS

BACKGROUND OF INVENTION

The present invention relates generally to x-ray generating devices, and more particularly, to an improved x-ray generating device having optimized record technique selection.

Fluoroscopy generally provides a real-time imaging mode for various x-ray procedures. Current radiography and fluoroscopy systems (R&F) include two independent exposure applications, record and fluoro. A user may adjust the initial tube peak voltage (kVp) in fluoro applications and set both tube voltage (kVp) and tube current (mA) in record applications. These initial values are set based on user preference or default values from a saved protocol database.

During a fluoro exposure, the tube current (mA) is adjusted first until a tube or patient dose limit is reached. Tube voltage (kVp) is then increased if necessary until proper image brightness (dose) is achieved. This sequence is repeated at the start of each fluoro exposure.

There are several parameters, which are controlled in order to effectively regulate exposure. These include kVp, mA, pulse width (exposure time), image quantum noise level (i.e., image receptor entrance exposure or entrance exposure rate). These also include focal spot, x-ray beam spectral quality and patient entrance radiation exposure rate (or Air Kerma). Each of these parameters has an optimal setting, which is unique for each of the procedure demands and patient sizes encountered.

During a record exposure, for example, the system may achieve proper brightness (dose) by applying the predefined tube voltage and tube current and increasing exposure time until the photocell reaches the desired brightness or until a time limit (backup time) is reached. Reaching backup time results in exposure termination and possible dark images. Any predefined record technique is based strictly on experience of the user.

Current procedures include the fluoroscopic sequence as a means of positioning a recording device through visualization of the internal anatomy of a patient. The recording device is then presented with the same view as in the fluoro mode, resulting in framed images prepared for diagnosis. This type of procedure generally requires a minimal amount of fluoroscopic time, which is typically less than five minutes.

Other procedures use the fluoroscopic mode as the primary mode for positioning instruments within the body, conducting medical intervention, and performing a medical diagnosis of a patient based on the fluoroscopic images. These procedures can be very lengthy and require a lengthy exposure to x-ray radiation.

There is currently no method for determining the current patient thickness and for the record technique and frame rate selected if an exposure will result in a backup time being reached. Additionally, no thermal prediction is possible based on an estimated exposure time. Any current prediction is based on the technique selected by the user and the maximum exposure time (backup time). This severely limits the exposure sequence because most exposures are actually less than the backup time.

It is generally desirable to improve the efficiency and performance of an x-ray generating device and to optimize exposures. Additionally, it is desirable to choose optimal techniques based on patient thickness and contrast being used.

SUMMARY OF INVENTION

In accordance with one aspect of the invention, a method for regulating a scan dosage includes starting from a default patient thickness. This default patient thickness defines the initial generator technique (kVp, mA, pw) and the target entrance dose. Following the exposure an actual technique and dose feedback signal is received and a true object size is estimated. An optimized technique (kVp, pw and target dose) is then defined based on the updated patient thickness. In addition the sensor feedback is compared to the target dose and the tube current is adjusted to match the target dose. After each exposure, the estimated patient thickness EPT is updated for next fluoro or record exposure.

In accordance with another aspect of the invention, a dose regulating system includes exposure management adapted to define an initial commanded technique signal based on a default patient size or a previous exposure. The generator is responsible for achieving the commanded technique and then on completion of the exposure, providing an actual technique signal. A current regulator is adapted to regulate tube current in response to the target entrance dose signal and dose feedback from the camera. A camera controller is adapted to independently control image brightness signal in response to the target entrance dose and measured image brightness. A neural net is adapted to estimate an object size based on the actual technique signal and dose feedback data. A technique selector is adapted to define an optimized generator technique for achieving a target image quality for a contrast material selection by the user.

One advantage of the present invention is that it estimates, during the fluoro exposure application, the current patient thickness and optimizes the technique selection based on this data for the contrast material being used in the procedure and reduces image quality variation. This information can be used for the next fluoro exposure or for a record exposure. This eliminates the time to start from user defined default values at the start of each fluoro exposure and the subsequent adjustment technique to reach target dose. The estimation of pulse width from this algorithm is also used to ensure correct frame rate before an exposure starts and to estimate tube capacity prior to an exposure.

Another advantage is that patient size estimation allows the user to focus on care of the patient instead of requiring intervention to adjust record technique. This results in higher productivity for the user and reduced exposure for the patient.

Other objects and advantages of the present invention will become apparent upon the following detailed description and appended claims, and upon reference to the accompanying drawings.

DETAILED DESCRIPTION

Figure 1:
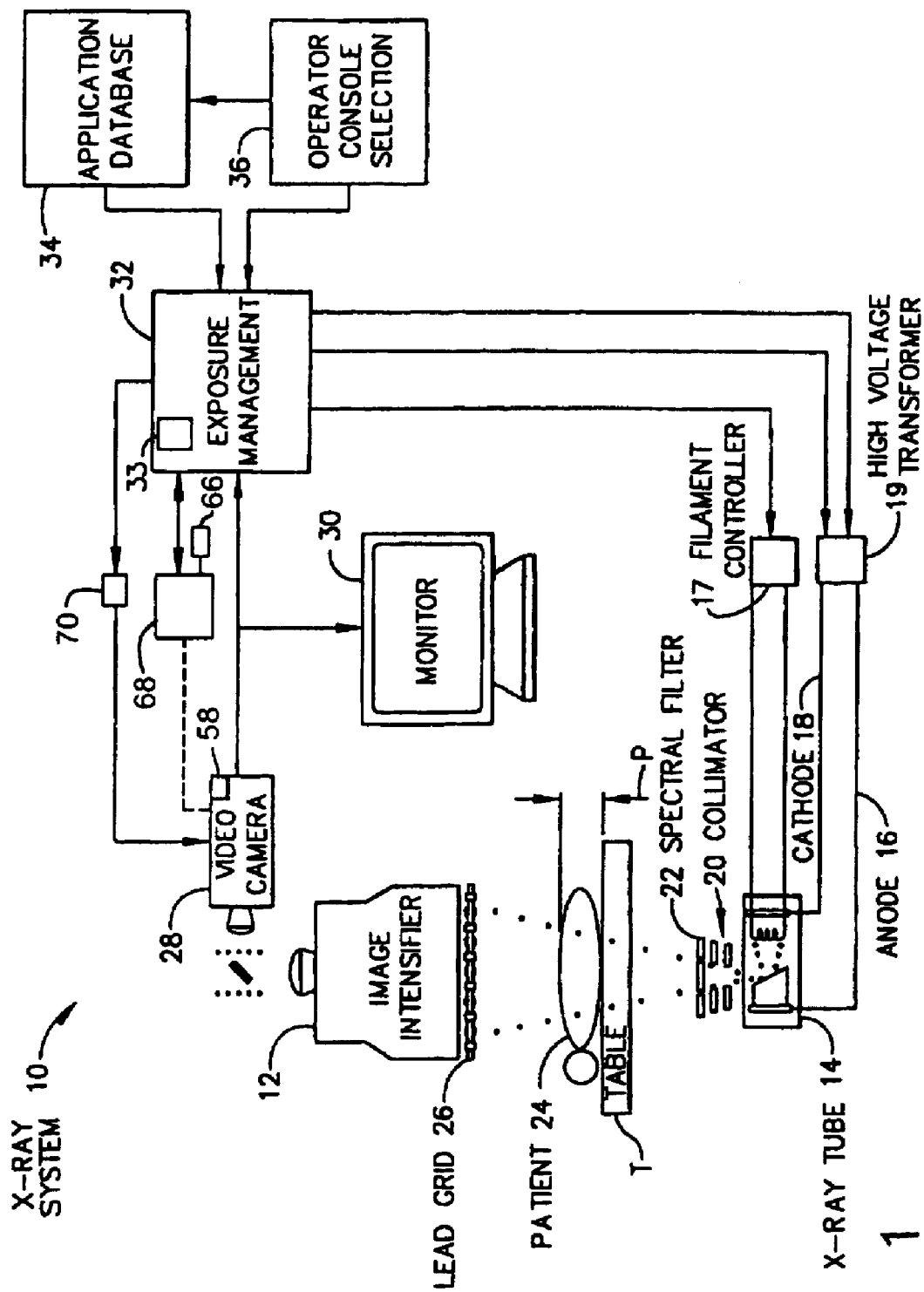
FIG. 1 is a block diagram of an x-ray system having both fluoroscopy and radioscopy capabilities in accordance with an embodiment of the present invention.

In the following figures the same reference numerals will be used to identify the same components in the various views. The x-ray system 10 is an example of an x-ray system wherein the present invention may be advantageously used and is not meant to be limiting.

Referring to the x-ray system 10 of FIG. 1, the image intensifier 12 receives x-rays generated from the x-ray tube 14. The tube 14 has associated anode 16 and cathode 18 structures. A filament controller 17 and high voltage transformer 19 are further coupled thereto. The Collimator 20 limits the size of the x-ray field to the desired patient area. X-rays are filtered by spectral filter 22 prior to transmission through an object under study, such as a human patient 24. Finally, the x-rays are received by an image intensifier 12 after passing through an anti-scatter grid 26. The image intensifier converts the x-rays to light which are transmitted through a camera 28 and output to monitor 30. Various control and selection features are associated with exposure management 32 (and control devices), application database 34 and operator console selection 36. The exposure management 32 includes several functions, each of which provide improved brightness control and technique selection automation and will be discussed later.

The x-ray system 10 also includes a generator 68 coupled to the exposure management 32 and a camera controller 58. A current regulator (mA regulator 66) is within the exposure management 32, and a count calculator 70 is coupled to the exposure management 32, the camera controller 58, and the generator 68. A photodiode is located on the output of the Image Intensifier. The light absorbed by the photodiode is amplified based on gain setting and then converted to a frequency signal. This signal is then transmitted real time during an exposure to the generator.

Desired levels of certain control variables for x-ray generation are based on present patient absorption characteristics. To automate this process, it is desirable to predict patient absorption during fluoroscopy. Typically, the region of interest during a procedure is confined in certain body areas where absorption characteristics remain constant. Cross-sectional thickness, a fair representative of patient absorption characteristics, and its prediction are used for automating the x-ray technique selection process.

Figure 2:
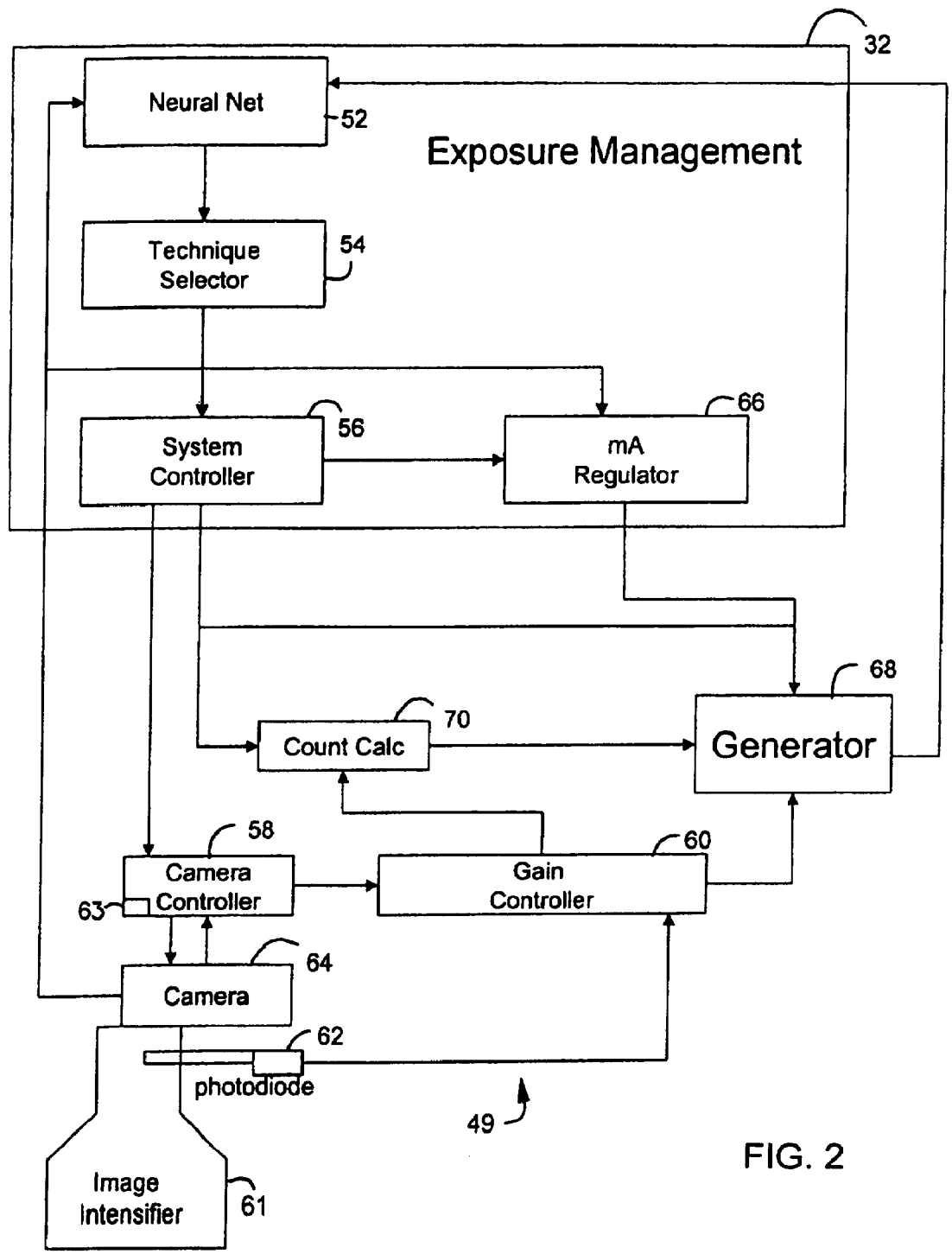
FIG. 2 is a block diagram of the fluoro and record sequences of the x-ray system of FIG. 1.

Block diagram 49 in FIG. 2 illustrates a method for regulating a scan dosage including the relationship between each of the aforementioned functions and the systems of FIG. 1 as a whole with a focus on a fluoro and a record sequence. In a preferred embodiment, the exposure management 32 includes several control devices including a size estimation neural net 52 (NN)-, a technique selector 54, and a system setup controller 56. The camera controller 58 is coupled to a photocell gain controller 60, a light sensor (photodiode) 62, and a light signal to frequency converter 63 and the camera 64. The camera controller 58, through the camera 64, determines an average brightness level of the image, which is used with a calibrated image system conversion factor to determine the effective entrance dose for the Image Intensifier 61. Camera control 58 may adjust, during the exposure sequence, the camera gain and the iris position, based on this average brightness, to ensure proper brightness to the monitor.

The fluoro sequence includes the system setup controller 56, which sets system defaults (kVp, mA, pw) and target entrance dose. Both the mA regulator 66 (current regulator) and the camera controller 58 receive the target entrance dose. The generator 68 receives the initial technique, which includes kVp, PW, and mA_initial.

During the exposure, the generator 68 achieves the initial default technique and provides an update of the actual exposure (kVp, PW, mAs) to the exposure management during the exposure sequence. The size estimation neural net 52 receives the actual technique signal and a dose feedback signal, generated after exposure. The neural net 52 estimates patient thickness and determines a patient thickness. The technique selector 54 receives the patient thickness value and determines which technique is appropriate for that patient thickness and selected contrast material. The system setup controller 56 issues this commanded technique signal to the generator. 68.

The mA regulator 66 and the camera controller 58 receive the target entrance dose signal. The mA regulator 66 also receives the dose feedback signal and compares it to the target value. A single parameter of tube current (mA) is adjusted to achieve the target dose. If mA cannot be increased due to patient dose or tube power limits, an effective patient thickness is applied to the value determined by the neural net 52.

The camera controller 58 receives the target dose signals from the system setup 56 to define the initial camera iris and gain settings. During an exposure, the camera controller 58 compares the average brightness feedback from the camera 64 to the target brightness and adjusts either the iris or camera gain to optimize output video signal level.

The technique selector specifies x-ray techniques at appropriate values for the contrast material. Procedure information, system selections and a default patient size are also used to set proper technique. This information is used with the active image quality trajectory (i.e., technique data tables) appropriate for the particular exam.

The optimal imaging technique is chosen from the loaded image quality trajectory as a function of relative patient size. The size is calculated within the size estimation neural net 52. The calculation includes data obtained during an acquisition by the neural net, which is trained to the x-ray spectra of the system. This enables the appropriate x-ray technique to commanded and maintained as the system is panned around the patient. Dynamic control of contrast, patient dose, image receptor exposure or exposure rate, image brightness, motion un-sharpness is responsively calculated. The aforementioned is accomplished by selecting optimal techniques with the trajectory and within the image control parameters set within either the exposure management 32 or the camera controller 58.

The neural network 52 or patient absorption calculator maps this complex input/output relationship. The parameters of a neural network are the weights that represent the strengths of the interconnections between nodes (or neurons), and the thresholds of some of the nodes. The neural net can have a feed-forward structure, that has just forward connections, or recurrent structures with reflexive, lateral, and backward connection weights as well.

The neural network 52 operates in two stages, including a learning (or training) phase and an operation phase. The purpose of the learning phase is to determine the appropriate parameters that will enable the network to function properly in the operation phase. The training algorithm is used in the learning phase. The neural network is trained to perform complex functions, especially non causal-effect relationships.

The prediction of patient thickness and patient dose level are based on the information of kVp and mA. It is also based on a dose feedback that represents detector entrance dose. It is also based on a conversion factor that is calibrated against reference level of brightness signal. Current system X-ray beam spectral quality (HVL and on the information of spectral filters, including copper filter thickness and aluminum filter thickness), is also used. Finally, the calibrated x-ray tube gain (mR/mAs) is used. Each input variable is normalized before being sent to the model. Each output variable needs to be "reverse-normalized" to get back to its true value. This neural net model is first trained on a subset of a big data set that is either generated by a physics-based model or collected in a lab environment. After the training session is successfully completed, the neural network is then tested on the remaining subset of the data set.

Each of the techniques, kVp optimized, Pulse Width optimized (PW), entrance dose optimized, and mA optimized are applied to the system generator 68 for the next exposure in the sequence. These procedures are repeated as often as required during an exposure sequence to maintain the desired image quality on the monitor.

The record sequence 51 includes the system setup controller 56. The generator 68 receives the technique of kVp, PW_est, and mA and a target count from a count calculator 70. The generator 68 still further receives a frequency signal from a camera control unit gain controller 60. The generator 68 responds to these signals by setting the target count threshold from the count calculator 70 and counting the pulses in the frequency signal until the count threshold is reached. When this occurs, the exposure is terminated and the actual technique (kVp and mAs) is determined and received by the exposure management 32.

The count calculator 70 receives the entrance target dose signal. The counter 70 also receives the voltage per pulse compensation signal from the photocell gain controller 60 and determines from the aforementioned signals the number of counts the current exposure will require and generates a target count.

The photocell gain controller 60 receives field of view (FOV) and collimator size information signals, as will be understood by one skilled in the art. The photocell gain controller 60 adjusts the photodiode gain to compensate for these. Based on the current photodiode gain, a dose/pulse is determined and provided to the count calculator.

The CCU gain controller 60 receives a brightness signal from the photodiode 62, which is typically located on near the output of the image intensifier 61. The CCU gain controller 60 is embodied as hardware, which adjust the photodiode gain for and transmits the frequency signal during the exposure. The CCU also during the exposure receives an average brightness value from the camera and camera controller 58 determines a dose feedback value based on this brightness, current camera and iris values, and the image intensifier conversion factor.

Exposure management 32 uses actual generator techniques and dose feedback during the fluoro exposure to determine a real time estimate of patient thickness. This information is then used to define an optimized fluoro and record techniques for the contrast material selected that will achieve target dose and image quality for the next exposure sequence. Optimized technique includes kVp, mA, spectral filter and exposure time (an estimate for record).

The estimated exposure time is used by the control system prior to start of record sequence to reduce frame rate if frame rate exceeds duty cycle and to determine tube thermal loading.

For record exposures, the photocell feedback is used to ensure that target entrance dose is achieved even if the user changes patient area without taking a fluoro exposure. The exposure limit (backup time) is based on frame rate.

Exposure management determines, during the fluoro sequence, an estimate of the patient size based on actual generator technique and image brightness data. Previous implementation of exposure management on cardiac systems used a model of the system response.

Patient size estimation is used to determine optimal record technique that can reach target dose levels with significantly reduced risk of reaching maximum exposure time (backup time).

Patient size estimation allows optimization of technique though trajectories based on contrast material used in R&F procedures (Iodine, Barium, air, etc.) to improve contrast and visibility. Use of trajectories based on contrast material and patient size estimation reduces variability in image quality due to user understanding of x-ray physics of contrast media being used for procedure. Trajectories developed for R&F procedures are optimized for contrast material.

Estimated exposure time allows system to determine prior to exposure to a patient if the current frame rate is achievable or if a slower frame rate is required. User may then abort the scanning sequence or continue the scanning sequence at slower frame rate. Current systems cannot determine, prior to exposure, if the frame rate selected will be possible. Estimates of exposure time can be used to provide to the user an estimate of the number of exposures that will be possible before a tube thermal limit is reached. Estimated exposure time may also be used to compensate for kVp tailing.

Estimated exposure time can also be used for error handling if the estimated exposure time has been exceeded for a record sequence. This information can be used for periodic maintenance or to remotely request, a service call.

Figure 3:
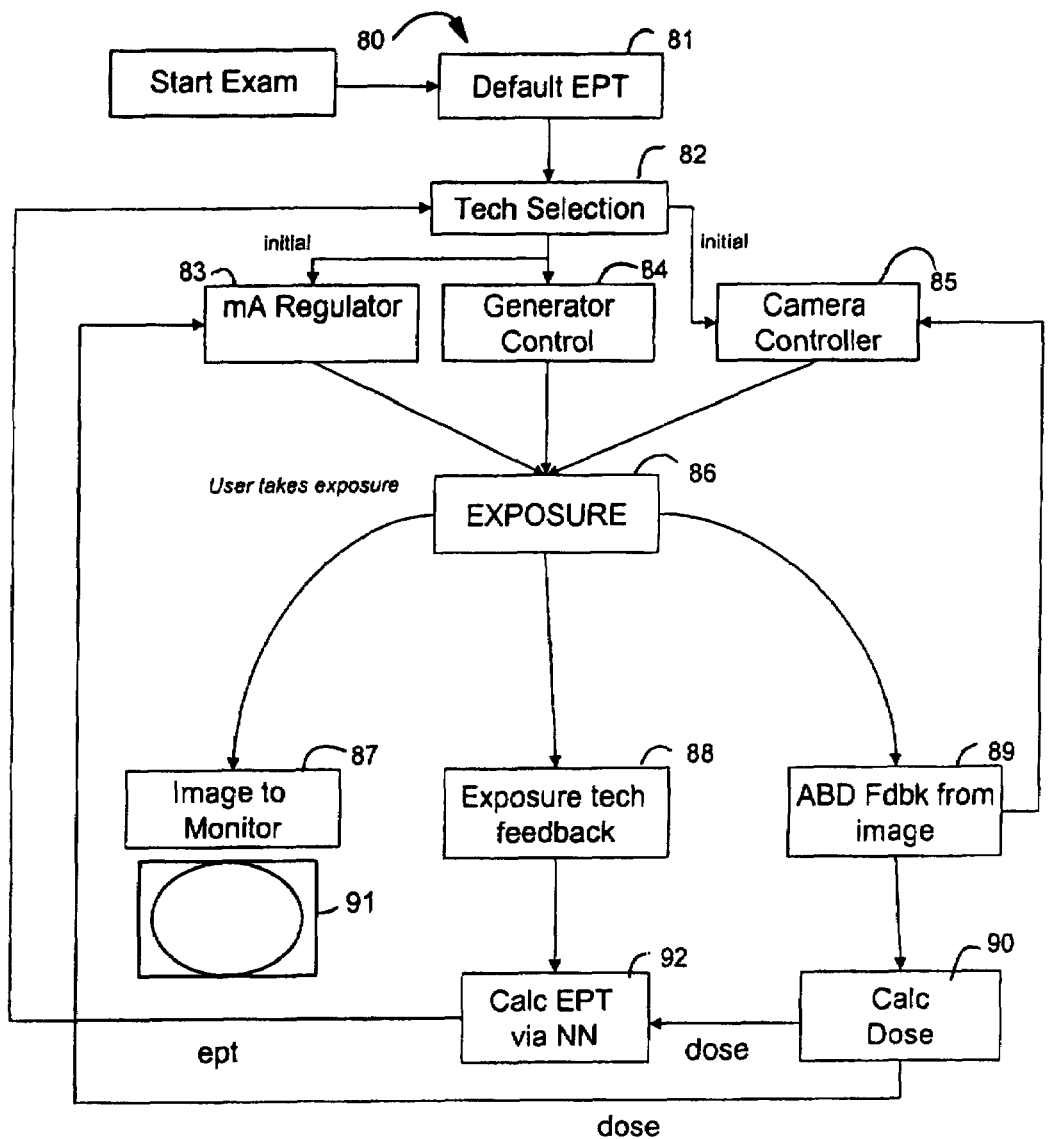
FIG. 3 is a logic flow diagram of a fluoro sequence in accordance with another embodiment of the present invention; and F

Referring to FIG. 3, a logic flow diagram 80 of a fluoro sequence in accordance with another embodiment of the present invention is illustrated. Logic starts in when the user starts the exam, the system setup within the exposure management activates, and the system defaults 81 are generated including the technique signal (received by the generator control 84) and the target entrance dose signal.

The mA regulator 83 and the camera setup 85 are activated and receive the target entrance dose signal. The mA regulator compares the actual dose in operation block 90 with the target dose. Tube current (mA) is then adjusted to achieve the target entrance dose. If a tube power limit or patient dose limit is reached, the mA regulator may increase the current patient thickness to allow system to reach target dose level.

The camera controller 85 receives the target entrance dose at the beginning of the exposure sequence 86 and will set the iris and camera gain based on the expected Image Intensifier entrance dose. During a sequence, the camera controller 85 will operate independently of the exposure management by adjusting the iris to ensure the average brightness of the image matches the target image brightness and sending the resultant image to a monitor 91 in operation block 87.

Otherwise, in operation block 90, average brightness of dose ABD feedback 89 is received in the exposure management 92 and mA regulator 83. In operation block 92, the size estimation neural net is activated, and the patient thickness signal is generated from analysis of the dose feedback and the actual technique signal (kVp, PW, mAs).

In operation blocks 88 and 82, the technique selector receives the patient thickness signal and selects an appropriate technique to tailor the scan to the patient thickness and generates a technique signal. The system setup then receives the technique signal and updates the technique in the generator for a more appropriate scan.

Figure 4:
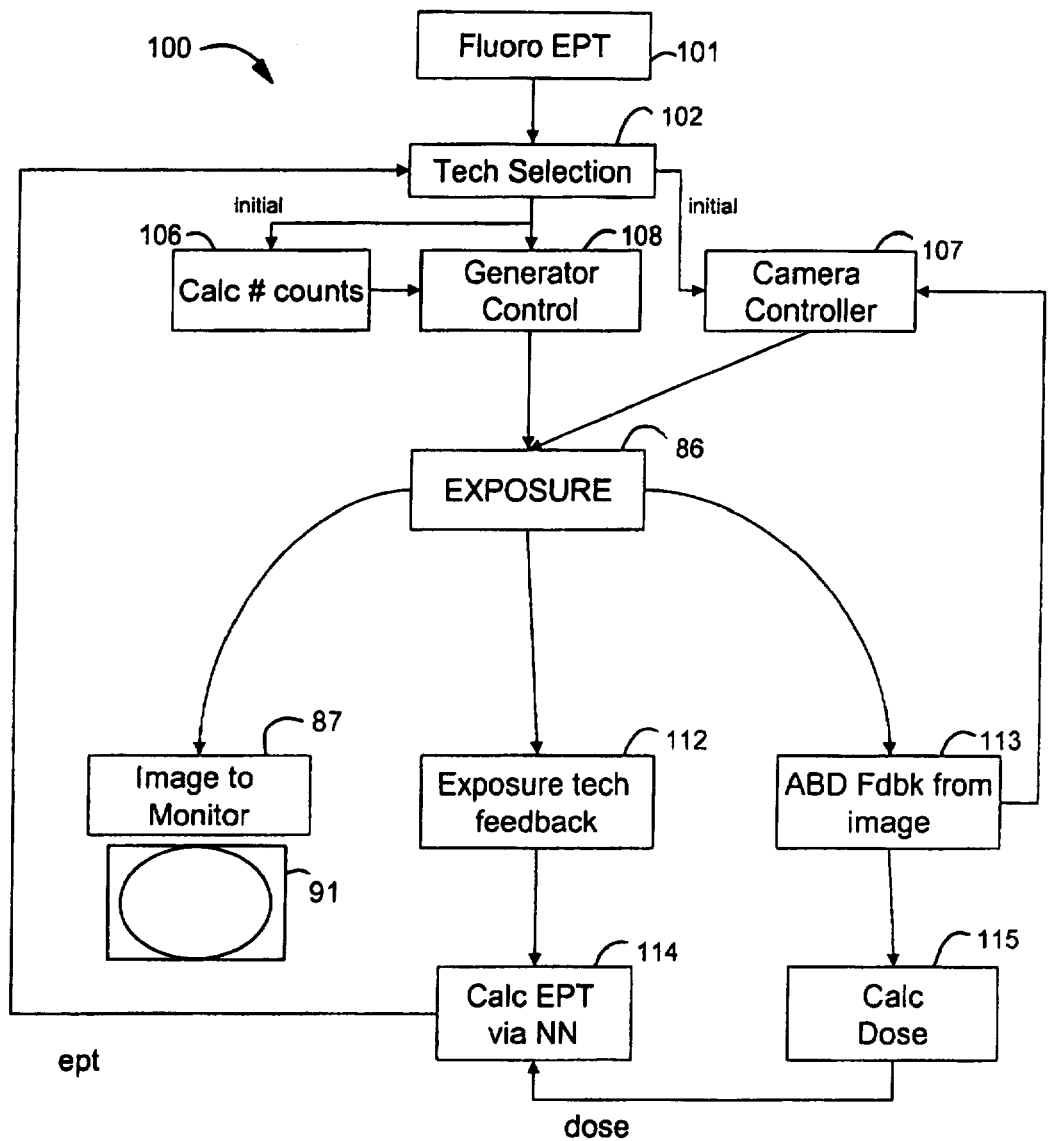
FIG. 4 is a logic flow diagram of a record sequence in accordance with another embodiment of the present invention.

FIG. 4, a logic flow diagram 100 of a record sequence, in accordance with another embodiment of the present invention, is illustrated. Logic starts in operation block 102, where the exposure management system setup activates. The system setup generates a technique signal and a target entrance dose signal based on previous fluoro exposure 101 or default patient thickness. In operation block 104, the photocell gain controller receives the field of view (FOV) and collimator size gains and generates the voltage per pulse compensation signal in response thereto. The CCU gain controller receives the brightness signal from photodiode in the camera and generates a frequency response signal.

In operation block 106, the count calculator activates and receives the target entrance dose signal and the voltage per pulse compensation signal from the photocell gain controller. The count calculator determines from these signals the number of frequency counts the exposure will require and determines the target count.

In operation block 108, generator functions are activated and a count threshold is set from the target count such that when the frequency response signal pulses are counted until the predetermined number of pulses has been reached. At this point, the record exposure is terminated.

The camera controller 107 is setup as part of the fluoro estimated patient thickness (EPT) and determines the average image brightness in operation block 113 and uses this value to adjust the camera gain for the next image and to calculate the dose in operation block 115.

In operation block 112 at the end of the exposure from operation block 86, the exposure management systems are activated to receive the actual technique (kVp, mAs) from the generator and determine the estimated patient thickness in operation block 114 from these techniques and the measured dose from the camera from operation block 115. The exposure image is sent to the monitor 91 in operation block 87.

In operation, a record and fluoro method includes generating an initial technique and for record, calculating a target count an exposure will require. In record, a frequency signal is then generated in response to a brightness signal, and frequency pulses from the frequency signal are counted until a threshold is met. The initial technique signal is updated with an actual technique signal, and a target entrance dose signal is generated. In fluoro, tube current is regulated in response to the target entrance dose signal. An object size is estimated based on the actual technique signal and image brightness data, and an optimized generator technique is then defined to achieve a target image quality for the next exposure While the invention has been described in connection with one or more embodiments, it should be understood that the invention is not limited to those embodiments. On the contrary, the invention is intended to cover all alternatives, modifications, and equivalents, as may be included within the spirit and scope of the appended claims.

What is claimed is:

1. A method for regulating a scan dosage comprising:
generating an initial technique command signal;
generating a target entrance dose signal;
upon completion of x-ray exposure, updating said initial technique signal with an actual technique signal and calculating a frequency pulse count required by an exposure;
regulating a tube current (mA) in response to said target entrance dose signal and a dose feedback;
controlling an output image brightness in response to said target entrance dose signal and an average brightness feedback signal from a camera;
compensating for image intensifier field of view and collimator size in said output image brightness;
estimating an object size based on said actual technique signal and image brightness data; and
defining an optimized generator technique to achieve a target image quality for a contrast material selected by a user.

2. The method of claim 1 wherein updating said initial technique signal with said actual technique signal further comprises generating a frequency signal in response to a brightness signal.

3. The method of claim 2 wherein updating said initial technique signal with said actual technique signal further comprises counting frequency pulses from said frequency signal until a threshold is met.

4. The method of claim 1 wherein defining an optimized generator technique to achieve a target image quality comprises optimizing the technique through trajectories based on contrast material used in radiography and fluoroscopy procedures.

5. The method of claim 1 wherein estimating an object size based on said actual technique signal and image brightness data comprises estimating an exposure time, wherein estimating said exposure time further comprises error handling when an estimated exposure time is exceeded for a record sequence.

6. A record and fluoro imaging method comprising:
generating an initial technique command signal;
for record exposure, calculating a frequency pulse count that an exposure will require;
for record exposure, generating a frequency signal in response to a brightness signal;
for record exposure, counting frequency pulses from said frequency signal until a threshold is met;
updating the commanded initial technique signal with an actual technique signal upon completion of said exposure;
generating a target entrance dose signal;
for fluoro exposure, regulating a current in response to said target entrance dose signal;
controlling an output image brightness in response to said target entrance dose signal and an average brightness feedback signal from a camera;
compensating for image intensifier field of view and collimator size in said output image brightness;
estimating an object size based on said actual technique signal and image brightness data; and
defining an optimized generator technique to achieve a target dose.

7. The method of claim 6 wherein defining an optimized generator technique to achieve a target comprises optimizing the technique though trajectories based on contrast material used in radiography and fluoroscopy procedures.

8. The method of claim 6 wherein estimating an object size based on said actual technique signal and image brightness data comprises estimating an exposure time, wherein estimating said exposure time further comprises error handling when an estimated exposure time is exceeded for a record sequence.

9. An x-ray system comprising:
an exposure management adapted to generate an initial technique signal, said exposure management further adapted to generate a target entrance dose signal;

a generator adapted to achieve said initial technique signal upon completion of exposure with an actual technique signal;

a current regulator adapted to regulate a tube current in response to said target entrance dose signal;

a camera controller adapted to control an output image brightness in response to said target entrance dose signal and a measured average image brightness;

a photodiode adapted to measure an exposure brightness;

a photocell gain controller adapted to set said photodiode gain based on an image intensifier field of view and collimator size;

a camera gain controller adapted to convert a brightness signal to a frequency signal;

a neural net adapted to estimate an object size based on said actual technique signal and image brightness data; and a technique selector adapted to define an optimized generator technique for achieving a target image quality.

10. The system of claim 9 wherein said generator is further adapted to count frequency pulses from said frequency signal until a threshold is met.

11. The system of claim 10 wherein said generator is further adapted to update said initial technique signal with said actual technique signal when said threshold is met.

12. The system of claim 9 further comprising a gain controller adapted to generate a frequency signal in response to a photodiode brightness signal.

13. The system of claim 9 further comprising a count calculator adapted to calculate a frequency pulse count that an exposure will require.

* * * * *